United States Patent [19]

Wilson

[11] 3,950,706

[45] Apr. 13, 1976

[54] VOLTAGE SWEEP GENERATOR WITH BISTABLE CURRENT SOURCE PROVIDING LINEAR SWEEP VOLTAGES

[75] Inventor: Homer M. Wilson, Houston, Tex.

[73] Assignee: Petrolite Corporation

[22] Filed: Aug. 9, 1974

[21] Appl. No.: 495,932

Related U.S. Application Data

[62] Division of Ser. No. 436,250, Jan. 24, 1974, Pat. No. 3,855,101.

[52] U.S. Cl. .............. 328/181; 307/228; 328/184
[51] Int. Cl.$^2$ ....................................... H03K 4/06
[58] Field of Search .................... 307/228, 229; 328/181–185

[56] References Cited
UNITED STATES PATENTS

| | | | |
|---|---|---|---|
| 3,350,651 | 10/1967 | Davis | 328/181 |
| 3,541,349 | 11/1970 | Bright et al. | 328/181 |
| 3,617,769 | 11/1971 | Hanson | 328/181 |
| 3,743,951 | 7/1973 | Carroll | 328/181 |
| 3,835,402 | 9/1974 | Kublick | 328/181 |

Primary Examiner—Stanley D. Miller, Jr.
Attorney, Agent, or Firm—Emil J. Bednar

[57] ABSTRACT

A voltage sweep generator provides a linear sweep voltage signal (triangular wave) between first and second magnitudes in the output circuit of an integrator driven by a control signal. The control signal is produced by a control network responsively to a control signal voltage of fixed magnitude but positive or negative in polarity. The linear sweep voltage signal correlates to reference voltages in a comparator with resultant limits switching signals. These switching signals activate a bistable amplifier to produce the control signal voltage of fixed magnitude and a polarity determinative of ramping up or down voltagewise.

The voltage sweep generator is especially useful in a novel dynamic analyzer for evaluation of voltage-current related properties in an external system and, in a particular application, to a unique potentistat employed in performing electrochemical analysis of corrosion phenomena in a test cell.

2 Claims, 1 Drawing Figure

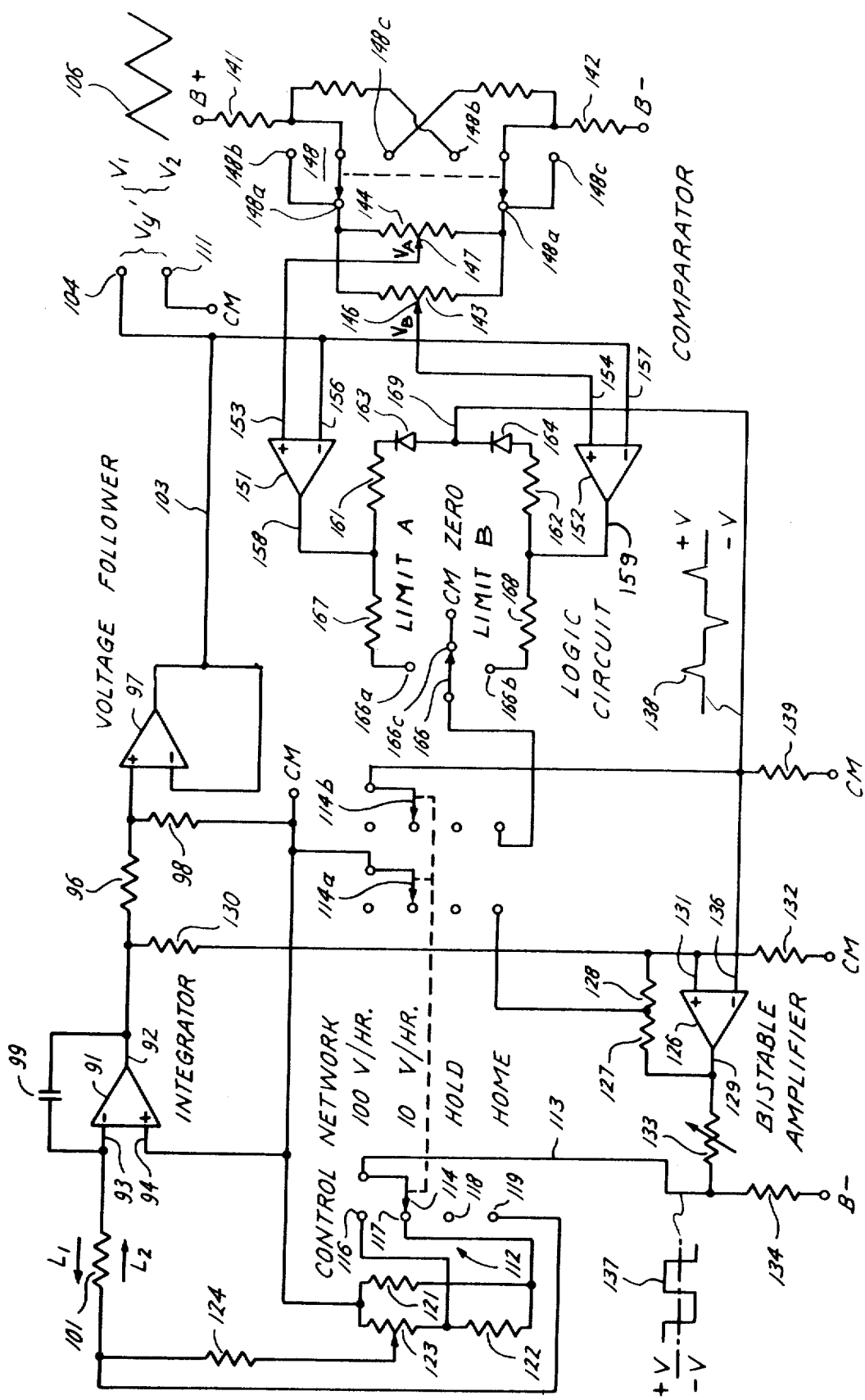

VOLTAGE SWEEP GENERATOR WITH BISTABLE CURRENT SOURCE PROVIDING LINEAR SWEEP VOLTAGES

This application is a division of Application Ser. No. 436,250, filed Jan. 24, 1974, now U.S. Pat. No. 3,855,101.

BACKGROUND OF THE INVENTION

1. Field of the Invention

This invention relates to measuring and testing electrochemical processes; and it relates particularly to instruments for the practice of electrochemical and electroanalytical techniques used in the study of corrosion processes in conductive media.

2. Description of the Prior Art

In the field of electrochemical and electroanalytical instruments and processes, many types of analyses can be performed in external systems which have voltage-current related properties. The study of corrosion phenomena is one such area. Other areas include, but are not limited to, the following: phase-sensitive AC, pulse, and DC polarography; anodic stripping analysis; cycling and potential sweep voltammetry; pH and specific ion measurement; direct potentiometry; controlled potential and controlled current electrolysis; chronopotentiometry; chronoamperometry; pulse response studies; electrical double layer capacitance measurements; itensiostatic, potentiostatic, and potentiokinetic methods for corrosion studies; and performing corrosion measurements as described in U.S. Pat. No. 3,101,406.

Instruments for practicing these analyses may be denoted, in a most general sense, as "potentiostats." Such instruments are arranged to produce and maintain a given voltage within the external system having voltage-current related properties by regulation of the current flowing therethrough. The potentiostatic instruments usually include a high impedance voltmeter for determining the maintained potential, a current source capable of maintaining a current flow to insure a constant value for the induced potential, and various auxiliary equipment which includes the cells, electrodes, and so forth, forming the external system, and various types of readout devices (ammeters, voltmeters, recorders, scopes, etc.). The auxiliary equipment can also include timers, recorders, and function generators capable of producing pulses, square waves, sawtooths and sine wave voltage sweeps. The readout means include oscilloscopes, various forms of wave analyzers, and impedance bridges.

The external system can be the classic types of electrochemical cells such as dropping mercury electrodes, hydrogen and glass reference electrodes, specific ion electrodes, metal electrodes and various combinations of such electrodes. These external systems all have a common characteristic at their electrical terminals. The external systems exhibit voltage-curent related properties at their terminals. In particular, a potential can be induced between a first pair of terminals, and other terminals are employed for passing a current through the cell which induces and maintains such potential. The magnitude and direction of the current flow and its function with time have a prescribed relationship to induced potential. These related properties of voltage and current are definitive of the electrochemical and electroanalytical composition of the cell.

The most common analysis of external systems having voltage-current related properties in aqueous media is voltammetry. In voltammetry, a pair of electrodes are employed for sensing the induced potential in the system. Other electrodes are employed for passing current through the conductive media for inducing the potential between the first electrode pair. The induced potential may be maintained constant for a given period of time, or it can be varied from a first, to a second, or even to a third, magnitude and varied at a constant rate with time, or with other functions with time such as exhibited by a sine wave or triangular wave.

Another electrochemical analysis of an external system found in measurements of corrosion phenomena is described in U.S. Pat. No. 3,406,101. In this patent, there is described an external system formed by a corrosion cell containing an aqueous corrodant in which are immersed three electrodes. Current is passed between two electrodes and induces a potential relative to a third electrode (reference). The current flow required to induce a certain potential change between the reference and one other electrode (test) is employed to determine the rate of corrosion which is occurring at the test electrode in the cell. Thus, the current flow in such a cell is the "readout" of the corrosion occurring at the test electrode.

The known external systems having voltage-current related properties have a plurality of terminals and conventionally have at least four terminals (e.g., two terminals to sense induced potential and two terminals to maintain current flow). For example, four-electrode conductivity cells are an external system having voltage-current related properties in which the potentiostatic instruments find ready application.

Prior art instruments employed in the electrochemical and electroanalytical field, particularly potentiostatic instruments, have provided useful results. However, these instruments left much to be desired in easy and reliable operation. First, the induced potential in the external system either had to be maintained at fixed levels for given lengths of time, and then changed with a square wave function to other levels in order to insure stable operation. Voltage sweeping has been attained, for the most part, by motor-driven rheostats which suffer from mechanical and electrical aberrations (i.e., nonlinear sweeing). In addition, should the voltage sweep direction of the induced potential be reversed, a time lag in voltage shift was experienced (i.e., discontinuous operation). A linear change in voltage within the external system is produced by a logarithmic change in current. Thus, a voltage shift of several tenths of a volt could change the current over several decades in magnitude. This linear-logarithmic property required complex switching equipment to insure even moderately accurate measurement in the magnitude of current flow. Furthermore, a third problem immediately arises. Since the data or readouts were in the linear voltage-amperage measurement system, correlating a certain voltage change to a certain current magnitude required a manual plot of volts and amperes upon log function graph paper or other such means. The voltage of the external system can be swept linearly over an extended range (0–10 volts) by the potentiostatic instrument. The current magnitude can change responsively over eight decades in less than 0.5 volts and is very difficult to obtain from linear data whose accuracy is good only for about four decades. Thus, the instrument operator was never sure that the voltage sweep information in his readout was directly correlatable to the related current magnitude. These operational difficulties in prior instruments have prevented the ready and accurate application of the electrochemical and electroanalytical techniques in evaluating corrosion phenomena, and other related analysis of external systems having voltage-current related properties. The present invention is directed towards an instrument which avoids these problems.

SUMMARY OF THE INVENTION

In accordance with this invention, there is provided a voltage sweep generator having an integrator receiving a control current signal and providing responsively in an output circuit a linear sweep voltage signal following a triangular wave between first and second voltage magnitudes. A control network provides the control current signal in response to a control signal voltage of fixed magnitude and positive or negative in polarity. A sweep voltage reference source generates first and second reference voltages corresponding to the first and second voltage magnitudes. Comparator means sample the linear sweep voltage signal, compares it with the first and second reference voltages, and generates several switching signals of a polarity indicative of which of the first and second reference voltages is approached by the linear sweep voltage signal. Bistable amplifier means receive successive swithcing signals from the comparator means and produces the control signal voltage applied to the control network with a fixed magnitude but changing in polarity on each successive switching signal whereby the linear sweep voltage is a triangular wave between first and second voltage magnitudes.

The present voltage sweep generator is of especial utility in a novel dynamic analyzer for evaluation of voltage-current related properties in an external system and, in a particular application, to a unique potentiostat employed in performing electrochemical analysis of corrosion phenomena in a test cell.

DESCRIPTION OF THE DRAWINGS

The FIGURE is a schematic of the voltage sweep generator of the present invention.

DESCRIPTION OF SPECIFIC EMBODIMENTS

In the drawing, there is shown a schematic of the voltage sweep generator 81 of the present invention. The voltage sweep generator 81 has one output 82 at circuit common and a second output 83. The voltage sweep generator 81 in a preferred embodiment produces a triangular wave sweep voltage which, as illustrated diagrammatically, ramps linearly between voltage magnitudes $V_1$, $V_2$. At any particular instant, this triangular sweep voltage has a magnitude and rate of change which may be indicated by $V_u'$.

The voltage sweep generator 81 is adjustable as to both magnitudes and polarity of $V_1$ and $V_2$, and also in the rate of sweep. Further, the voltage sweep generator 81 can be adjusted as to sweep only from voltage $V_2$ to $V_1$, or $V_1$ to $V_2$, or any portion thereof, or to sweep continuously between these two values over any practical time limit. For example, sweep rate may be the completion of one full triangular wave in 24 hours or in 10 minutes. Irrespective of the sweeping rate, the output of the voltage sweep generator 81 is linear.

In particular, the voltage sweep generator 81 of the present invention can be arranged to have voltage sweep rate limits between 0.01 volts per hour to 100.0 volts per hour; it can hold any particular set voltage $V_u'$; or it can sweep continuously between the voltage limits $V_1$ and $V_2$, or from zero to either one or the other of these voltage magnitudes. Thus, the voltage sweep generator 81 can produce a linear sweep voltage signal $V_u'$ from a first magnitude $V_1$ to a second magnitude $V_2$, and preferably it provides a triangular wave sweeping voltage signal.

The voltage sweep generator 81 is shown in circuitry detail. The generator 81 includes an integrator having an output circuit carrying the linear sweep voltage signal produced in response to a control current signal. A control network provides the control current signal upon receipt of a control signal voltage of fixed magnitude and positive or negative in polarity. A sweep reference voltage source provides first and second reference voltages. The linear sweep signal is correlated to the reference voltages in a comparator which generates switching signals at the sweep signal reaching each of the reference voltages. The switching signals are applied to a bistable amplifier which produces the control signal voltage of fixed magnitude but alternates in positive and negative polarity. The polarity of the control signal voltage determines whether the linear sweep voltage ramps up or down voltagewise.

More particularly, an integrator 91 receives a current control signal and provides responsively in an output circuit 92 a linear sweep voltage signal. For this purpose, the integrator 91 can be a differential input amplifier having the usual connections with the power supply 28, a first input 93 receives the control current signal, and a second input 94 is at circuit common. The output 92 connects through voltage dividing resistors 96 and 98 to a voltage follower 97. The capacitor 99 connects between the input 93 and output 92 for providing the integrating function. The input 94 connects to circuit common. As the potential at input 93 tends to change through the flow of current through resistor 101 into the capacitor 99, the output 92 swings voltagewise to hold input 93 at circuit common. If the current at the input 93 is of uniform magnitude, the voltage change at the output 92 is a linear function. For example, the control current signal flowing through resistance 101 to the input 93 is indicated by $i_2$. As this current charges the capacitor 99, the output 92 changes in a negative direction with a linear function. Conversely, a current flowing from input 93 through the protective resistor 101 is indicated by $i_1$ and produces a positive linear voltage change at the output 92. The conductor 103 from the voltage follower 97 is applied to terminal 104 and by suitable connection to the input 37 of the error signal amplifier 19. The terminal 111 of the voltage sweep generator 81 is at circuit common. The terminals 104 and 111 carry the linear sweep voltage $V_u'$ represented as triangular wave 106 which ramps between voltage magnitudes $V_1$ and $V_2$. The directional current flow of the control current signal $i_1$ or $i_2$ in the resistor 101 determines whether the linear sweep voltage $V_u'$ is increasing or decreasing in magnitude. Therefore, the control current signal is derived from a relatively stable source and, in the present voltage sweep generator 81, a control network 112 is employed for this purpose.

The control network 112 is comprised of a conductor 113 carrying a finite positive or negative control signal voltage magnitude. The source of this control signal voltage will be described hereinafter. The control signal voltage is applied through movable switch segment 114 to a plurality of contacts 116, 117, 118 and 119. These contacts are connected into a resistance network formed of fixed resistors 121 and 122, a variable 123, and connected through a series resistance 124 to the resistor 101 at input 93 of the integrator 91. These network resistances in the control network 112 provide a stable and selectable impedance divider whereby the positive or negative control signal voltage is converted into a finite control current signal which flows through the resistance 101. The several switch controls provide for selecting the rate of change of the linear sweep voltage. For example, the switch at contact 116 selects a sweep rate of zero to 100 volts per hour; at contact 117, a sweep rate of zero to 10 volts per hour; and contacts 118 and 119 provide functions in the analyzer, which will be described in greater detail hereafter, of "Hold" at a selected $V_u'$ and "Home" to $V_1$ or $V_2$. Sweep rates at contacts 116 and 117 are determined by variable resistor 123.

The control signal voltage applied to the control network 112 may be either positive or negative in polarity to determine, respectively, whether the linear sweep voltage is increasing or decreasing in magnitude. In accordance with the preferred embodiment of this invention, the control signal voltage is made alternatively positive and negative in polarity so as to produce a triangular linear sweep voltage signal 106 in the output 92 of the integrator 91. The control network 112 in conjunction with the control voltage signal provides for regulating the magnitude and direction of current flow of the control current signal through the resistor 101, thereby determining the rate of increasing or decreasing of voltage in the linear sweep voltage signal in output 92.

The control voltage signal in the conductor 113 is produced in a novel fashion with alternate changes in polarity but of a preset fixed and stable magnitude. For example, the control signal voltage may be a positive or a negative 10 volts. The control signal voltage is provided by a bistable amplifier 126 which has the usual connections to the power supply 28. Preferably, the bistable amplifier 126 is a differential input amplifier having a component gain of about 50,000. However, a positive feedback circuit of resistors 127 and 128 between its output 129 and first input 131 provides the feedback necessary to obtain a bistable operation. The voltage divider of resistors 130 and 132 provides a portion of the integrator output 92 voltage at the input 131 of the bistable amplifier 126. The bistable amplifier 126 switches from saturation from one polarity voltage limit to the other polarity voltage limit when the voltage difference becomes zero between inputs 131 and 136. This operation results from positive feedback to input 131 from the output 129 and the high internal gain of amplifier 126. The resistors 133 and 134 compensate for any difference in the saturation characteristic of the bistable amplifier 126 about zero output voltage. The bistable amplifier 126, when correctly adjusted, causes the control signal voltage to swing to and remain at one of two equal magnitudes of voltage but opposite in polarity. This function is indicated by the graphic display 137 as shifting between +V and −V about a zero voltage magnitude.

The bistable amplifier 126 is switched from one to the other polarity control voltage signal by successive switching signals 138 applied to input 136. The input 136 connects to circuit common by a resistor 139 and receives the switching signal shown in the graphic display 138. Each successive switching signal upon the input 136 causes the output 129 to move from one to the other polarity of the control signal voltage. The bistable amplifier 126 switches its output 129 between absolute and stable finite magnitudes equal but opposite in polarity upon receipt of successive switching signals at the input 136 irrespective of the magntidues of such switching signal.

The switching signals can be of opposite polarity as idicated by the diagrammatic representation 138. The switching signals may be of any duration or of uniform or nonuniform magnitude as long as they are sufficient in both characteristics of polarity and voltage magnitude to cause the inputs 131 and 136 of the amplifier 126 to become equal potentialwise. With the proper switching signal, the positive feedback about the amplifier 126 causes the output 129 to shift so that the control signal voltage is at one of the limits +V and −V set by the variable resistance 133. Immediately after shifting directionally through zero, the positive feedback of the bistable amplifier 126 holds the output 129 to maintain such voltage limit, +V or −V, until the next succeeding switching signal of opposite polarity. For example, the first switching signal in the diagram 138 is indicated as positive going. This corresponds to the control signal voltage in the diagram 137 being switched in a negative direction to the limit of negative polarity (−V). The next succeeding switching signal is negative going and causes the control signal voltage 137 to be switched to the limit of positive polarity, +V. The control signal voltage remains at each such magnitude and polarity until the next succeeding switching signal of opposite polarity.

In the voltage sweep generator 81, the switching signals occur in exact timing to the linear sweep voltage between terminals 104 and 111 reaching the magnitudes $V_1$ and $V_2$, respectively. As the triangular wave sweep voltage reaches the magnitude $V_1$, the switching signal may be of negative polarity, and upon reaching the magnitude $V_2$ may be of positive polarity. For this purpose, the voltage sweep generator 81 includes a comparator for determining when the triangular wave sweep voltage reaches one of the magnitudes $V_1$ or $V_2$ and produces the switching signals at the precise timing when these values are reached. For this purpose, the comparator samples the linear sweep voltage signal at the terminal 104 and compares this sweep voltage signal with first and second reference voltages $V_A$ and $V_B$, respectively, defining particular magnitudes of the sweep voltage limits $V_1$ and $V_2$ as indicated in the graphic display 106. Precisely as each of the sweep voltage magnitudes $V_1$ and $V_2$ are reached in reference respectively to the first and second reference voltages, successive switching signals occur with opposite polarities.

The first and second reference voltages $V_A$ and $V_B$ are obtained from any suitable source such as a resistance divider network connected to the powder supply 28. This resistance network includes dropping resistors 141 and 142 which connect across paralleled potentiometers 143 and 144. The value of these resistances are so arranged that the first and second reference voltages $V_A$ and $V_B$ (relative to circuit common) appear at the movable contacts 146 and 147 on these potentiometers. With the arrangement shown, $V_1$ and $V_2$ may be of any magnitude and any polarity relative to one another. For example, $V_1$ and $V_2$ may be of equal magnitude but opposite in polarity. Alternatively, $V_1$ and $V_2$ may be both positive in value, but of different magnitudes. Alternatively, $V_1$ and $V_2$ may be negative in value and of different magnitudes. Also, $V_A$ and $V_B$ may be taken at either one of the movable contacts 146 and 147. In order to provide an instant reversal of sweep direction, the resistor network is interconnected through a momentary double-pole, triple-throw switch 148. The switch 148 at terminal 148a is the normal switch position where both reference voltages $V_A$ and $V_B$ are available at the movable contacts 146 and 147. Placing the switch 148 into the position 148b substitutes new reference voltage limits that are both to one side of $V_u'$ voltagewise. Moving the switch 148 to the position 148c substitutes new reference voltage limits that are both to the other side of $V_u'$ voltagewise. Thus, positions 148b and 148c permit sweep direction reversal. Returning the switch to position 148a returns the voltage sweep limits to $V_A$ and $V_B$. If $V_u'$ resides between $V_A$ and $V_B$, the sweep direction will not be reversed. Thus, there is a feature of selected sweep direction reversal in the present voltage sweep generator without disturbing the voltage sweep limits $V_1$ and $V_2$.

The comparator has differential input amplifiers 151 and 152 with their inputs receiving the first and second reference voltages and the sweep voltage signal at the terminal 104. The amplifier 151 and 152 should have relatively high component gains of approximately 50,000 and are adapted with zero input voltage to move from one saturated state to the other saturated state of opposite polarity and then returns into the first saturated state. With this arrangement, high sensitivity to small potential differences between the voltage limits $V_1$ and $V_2$ of the linear sweep voltage signal can be readily compared to the first and second reference voltages. The amplifier 151 has a first input 153 connected to the movable contact 147 to receive the first reference voltage. The amplifier 152 has an input 154 connected to the movable contact 146 to receive the second reference voltage. The remaining inputs 156 and 157 of these amplifiers are connected together and to the terminal 104 to receive the linear sweep voltage signal for comparison purposes. As the sweep voltage magnitudes $V_1$ and $V_2$ are approached closely by the linear sweep voltage at the terminal 104, the voltages between the inputs of one of the amplifiers 151 and 152 approach a zero voltage signal differential and this amplifier's output swings from one saturated state to the opposite polarity saturated state. The outputs 158 or 159 of the amplifiers 151 and 152, respectively, move suddenly voltagewise to preset magnitudes that are determined by an output resistor-diode network. As a result, the active amplifier reverses state and returns to its original saturated state. For this purpose, the outputs 158 and 159 connect through series resistors 161 and 162, and rectifiers 163 and 164, to a conductor 169 which connects with the input 136 of the bistable amplifier 126. The rectifiers 163 and 164 are series connected between the outputs 158 and 159. When the voltage magnitude limits $V_1$ or $V_2$ for the linear sweep voltage signal reside between the first or second reference voltages $V_A$ and $V_B$, the amplifiers 151 and 152 have their outputs 158 and 159 shifted voltagewise in such a manner that the rectifiers 163 and 164 are both biased into a conducting or nonconducting state. When the linear sweep voltage signal at the terminal 104 reaches one of the first or second voltage magnitudes $V_1$ or $V_2$, one of the rectifiers is biased to a conducting state and the other of the rectifiers is biased into a nonconducting state whereby a voltage signal produces the switching signal on conductor 169. These switching signals alternate in polarity, but each of them occurs precisely as the linear sweep voltage reaches one of the first and second voltage magnitudes $V_1$ and $V_2$. The resistances and rectifiers in the outputs of the comparator amplifiers 151 and 152 are a logic circuit for generating the switching signals of alternate polarity in succession.

The comparator with the switch 114 in the "Home" position 119 may be employed for causing the linear sweep voltage signal to go to either of reference voltage sweep limits $V_A$ or $V_B$. For this purpose, a switch 166 is employed in a single-pole, triple-throw function. The switch in position 166a connects through a load resistor 167 to the output 158, and in position 166b connects through a resistor 168 to the output 159, and in central position 166c connects to circuit common. In the normal operating position 166c, the voltage sweep generator 81 can be zeroed under static conditions at the "Hold" position of switch 114 at contact 118. In the position 166a, the reference sweep voltage $V_A$ will appear at terminal 104. In position 166b, the reference sweep voltage $V_B$ appears at the terminal 104. In position 166c, zero voltage appears at terminal 104. During normal operation of the instrument with the switch 114 at the contacts 116 or 117, the switch 166 is inactive. However, the switch 114 at the contact 119 places the sweep voltage generator 81 into the "Home" function. Also, switch 114a in "Home" removes the positive feedback from amplifier 126 by shorting the juncture of resistors 127 and 128 to circuit common. The switch 114 at contact 118 "Hold" will hold the sweep voltage signal at its instant magnitude $V_u'$. The switch 114 also has sections 114a and 114b which function exactly as previously described. In the "Home" position, the switch 114b connects to the switch 166 and the conductor 169, and with input 136 of the bistable amplifier 126.

The comparator in the present voltage sweep generator 81 is of great advantage in providing several unique sweep generator functions which have been heretofore described. The control current signal from control network 112 that is applied to the integrator 91 is always stable and of a preset magnitude even though it undergoes alternate directional changes in flow through the resistor 101. The resistor 139 returns the logic circuit to circuit common.

In the present voltage sweep generator 81, placing the switch 114 into the "Hold" function terminates the application of the control signal voltage on the conductor 113 into the control network 112. At such time, the integrator 91 ceases to receive a control signal current through the resistor 101 and integration stops within capacitor 99. As a result, the linear sweep voltage $V_u'$ is held at the potential last achieved before the switch 114 was moved into the "Hold" position. Thus, a fixed sweep voltage $V_u'$ is available at terminal 104 for reference setting or for other purposes.

Various modifications and alterations in the described voltage sweep generator are apparent to those skilled in the art from the foregoing description which do not depart from the spirit of the invention. For this reason, these changes in elements and functioning are desired to be included within the scope of the present invention. The appended claims define the present invention and the foregoing description is to be employed for setting forth the specific embodiments as illustrative in nature.

What is claimed is:

1. A voltage sweep generator comprising:
   a. an integrator receiving a control current signal and providing responsively in an output circuit a linear sweep voltage signal following a triangular wave between first and second voltage magnitudes;
   b. a control network providing the control current signal to said integrator in response to a control signal voltage of fixed magnitude and positive or negative in polarity;
   c. a sweep voltage reference source for providing first and second reference voltages corresponding to the first and second voltage magnitudes;
   d. comparator means for sampling the linear sweep voltage signal and comparing same with the first and second reference voltages, and said comparator means generating several switching signals of a polarity indicative of which of the first and second reference voltages is approached by the linear sweep voltage signal, and said comparator means including a pair of differential amplifiers each having one input connected to the output circuit of said integrator and each having another input receiving one of said first and second reference voltages, the outputs of said differential amplifiers connected to a logic circuit, said logic circuit receiving output signals from said differential amplifiers which signals change in magnitude as the linear sweep voltage approaches one of said first and second voltage magnitudes, said logic circuit producing successively said switching signals of alternate positive and negative polarity with a fixed relationship to each of said first and second voltage magnitudes and each signal corresponding in timing to the linear sweep voltage signal reaching one of said first and second voltage magnitudes; and
   e. bistable amplifiers means receiving successive switching signals from said comparator means and producing the control signal voltage applied to said control network with a fixed magnitude but changing in polarity on each successive switching signal whereby said linear sweep voltage is a triangular wave between first and second voltage magnitudes.

2. The voltage sweep generator of claim 1 wherein said logic circuit comprises a pair of rectifier means connected for series current flow between the outputs of said differential amplifiers and a switching signal output circuit connected to the juncture of said rectifier means and biasing means in series with each rectifier means, and the outputs of both rectifier means are biased into either a conducting or nonconducting state for all output signals from said differential amplifiers when the linear sweep voltage is between said first and second voltage magnitudes and for output signals from said differential amplifier as the linear sweep voltage reaches one of said first and second voltage magnitudes, one of said rectifier means is biased into a conducting state and the other of said rectifier means is biased into a nonconducting state whereby one of said switching signals is applied to said switching signal output circuit, and each said switching signal being timed to the linear sweep voltage signal reaching one of said first and second voltage magnitudes and the polarity of each said switching signal having a fixed relationship to which of said first and second voltage magnitudes has been reached by the linear sweep voltage signal.

* * * * *